United States Patent
Clark (10) Patent No.: US 7,318,001 B2
(45) Date of Patent: Jan. 8, 2008

(54) METHOD AND APPARATUS FOR COLLECTING DATA FOR DETECTING AND LOCATING DISTURBANCES

(75) Inventor: James Alden Clark, Columbia City, OR (US)

(73) Assignee: CNV Technologies, LLC, Columbia City, OR (US)

( * ) Notice: Subject to any disclaimer, the term of this patent is extended or adjusted under 35 U.S.C. 154(b) by 9 days.

(21) Appl. No.: 11/121,744

(22) Filed: May 3, 2005

(65) Prior Publication Data

US 2006/0265164 A1  Nov. 23, 2006

(51) Int. Cl.
*G01P 21/00* (2006.01)
*G06F 15/00* (2006.01)

(52) U.S. Cl. .................................. 702/94; 702/152
(58) Field of Classification Search ............ 702/94, 702/95, 150–154
See application file for complete search history.

(56) References Cited

U.S. PATENT DOCUMENTS

| | | | |
|---|---|---|---|
| 3,509,555 A | 4/1970 | Loughlin et al. ............ 341/15 |
| 4,263,551 A | 4/1981 | Gregory et al. | |
| 5,353,354 A | 10/1994 | Keller et al. | |
| 5,842,986 A | 12/1998 | Avrin et al. | |
| 6,026,818 A | 2/2000 | Blair et al. | |
| 6,092,928 A | 7/2000 | Mattson et al. | |
| 6,122,538 A | 9/2000 | Sliwa, Jr. et al. | |
| 6,466,205 B2 | 10/2002 | Simpson et al. | |
| 6,507,669 B1 | 1/2003 | Klassen | |
| 6,687,531 B1 | 2/2004 | Ferre et al. | |
| 6,691,042 B2 | 2/2004 | Weng et al. | |
| 6,705,522 B2 | 3/2004 | Gershman et al. | |
| 6,737,591 B1 | 5/2004 | Lapstun et al. ........... 178/19.05 |
| 6,861,954 B2 | 3/2005 | Levin | |
| 7,009,561 B2* | 3/2006 | Menache et al. ............ 342/463 |
| 7,019,650 B2 | 3/2006 | Volpi et al. .............. 340/572.1 |
| 2003/0066537 A1 | 4/2003 | Fabian et al. | |
| 2003/0105394 A1 | 6/2003 | Fabian et al. | |
| 2004/0260174 A1 | 12/2004 | Keene | |
| 2006/0077036 A1 | 4/2006 | Roemerman et al. ...... 340/5.61 |
| 2006/0212260 A1* | 9/2006 | Kopelman et al. .......... 702/152 |

\* cited by examiner

*Primary Examiner*—Michael Nghiem
(74) *Attorney, Agent, or Firm*—Portland Intellectual Property, LLC (57) ABSTRACT

A method and apparatus for collecting data for detecting and locating disturbances. A plurality of distinct regions of the space are identified, and, preferably, a hand-held device adapted for sensing positions of the device and respective representations of a field parameter at the positions is used. The positions are quantized within the regions and the corresponding representations within a region are combined. Separate scans are used to obtain baseline and detection scan results corresponding to the regions. The baseline and detection scan results are compared within a region, and the results of the comparison are used to produce scan results from which can be discerned whether a disturbance has occurred within the region. A triangulation is performed for determining the location of the disturbance, preferably using combinations of indeterminate sets of the scan results.

65 Claims, 7 Drawing Sheets

METHOD AND APPARATUS FOR COLLECTING DATA FOR DETECTING AND LOCATING DISTURBANCES

FIELD OF THE INVENTION

The present invention relates generally to a method and apparatus for collecting data, which may be used for detecting and locating disturbances, such as objects or radiations. More particularly, the invention relates to use of a hand-held sensing device capable of sensing its own position in space as well as a magnitude of the disturbance at each of several positions for collecting and evaluating such data. Still more particularly, the invention relates to detecting and locating disturbances providing weak signals or that are weakly interacting. In this latter connection, the invention has a very particular relation to detecting and locating medical objects unintentionally left behind inside the body cavity of a medical patient.

BACKGROUND

There are many contexts in which it is desired to ascertain the presence of a concealed object. In medical practice particularly, and even more particularly in surgical practice, there is a critical need to track the locations of medical tools, devices, aids, materials, and other objects. And the most critical need of all is to ensure that no such medical objects are unintentionally left behind inside a patient's body cavity after a surgical procedure has been completed.

For providing best estimates of the position or location of an object, detectors adapted for sensing the object are preferably fixed in space at known positions in the space. To most closely realize this goal when using a movable detector, the detector is preferably moved automatically and repeatably by robotic devices to ensure that measurements correspond to specific points in space. However, in the medical theater, there are typically a number of lines and wires connecting the patient to various devices and implements that are present in the vicinity, there may be a number of surgeons and other personnel standing in the vicinity, and there is an abundance of equipment, trays and carts for holding tools in proximity to this personnel, so that the area around the patient's body is cramped and difficult to negotiate. For these reasons as well as others, it has been found to be impractical to use fixed sensing devices, or a sensing device that is moved on, e.g., a track, or with a pre-programmed robotic arm, for sensing medical objects inside a patient.

Position sensing using hand-held devices is known in medical imaging, and position tracking has been used to track the movements of surgical instruments. For example, Sliwa Jr., et al., U.S. Pat. No. 6,122,538 ("the '538 Patent"), refers to a movable ultrasound transducer probe utilizing a set of translational accelerometers for measuring both translational and angular accelerations. Position and angle changes are deduced by double integration. However, the '538 Patent acknowledges that the system is subject to substantial inaccuracies, making it difficult or impossible to return to a previous scan position. Hence, the '538 Patent proposes a hybrid system that also incorporates a gyroscopic sensor array having three orthogonal gyroscopes. This type of device is commonly referred to in the art as an "inertial guidance system," although the system need not be used for guidance and can be used, as suggested in the above reference, merely for sensing.

Ferre et al., U.S. Pat. No. 6,687,531 ("the '531 Patent"), provides an example of tracking the movements of a surgical instrument. In one embodiment, the location of the instrument may be determined with respect to fixed transmitters (or receivers) attached to the patient's head by triangulation. In another embodiment, a field is generated using three orthogonally disposed magnetic dipoles, and the known near-field characteristics are used for position detection.

Neither of the aforementioned systems is suited to searching for, or detecting the location of, concealed and unknown objects. The '538 Patent merely detects the location of a probe that is in the possession of a user of the system. The probe is not used to acquire data about another object having unknown characteristics. The '531 Patent merely tracks the location of a probe as it moves in the body. The standard prior art methodologies for tracking the location of surgical instruments or other medical objects left in a patient's body are either to X-ray the patient, which is undesirable for obvious reasons, or simply to count the objects used during the surgery before and after the surgery.

Some more sophisticated approaches for detecting medical objects in a patient's body cavity have been proposed. These fall into two basic categories, depending on the constitution of the medical object. On the one hand, metal medical objects can be detected using, essentially, a metal detector. Avrin et al., U.S. Pat. No. 5,842,986 ("the '986 Patent"), is exemplary. On the other hand, some medical objects, such as sponges, do not interact with electromagnetic fields. However, such objects can be tagged with RFID (acronym for "radio frequency identification") tags and the tags can be stimulated to produce an output that can be detected. Blair et al., U.S. Pat. No. 6,026,818 ("the '818 Patent"), is exemplary of this approach.

Hobbyists use metal detectors for discerning the presence of buried coins and other artifacts, and metal detectors are also used, now ubiquitously, in security systems for discerning the presence of concealed weapons. Metal detectors may sense radiation reflected or otherwise transmitted from the object, or may sense a change in the inductance of a coil that is induced by the presence of a nearby metal object. The '986 Patent in particular proposes applying a low strength, time varying magnetic field to a screening region of a body and sensing a responsive magnetic field from a retained ferrous body within the screening region. As in standard metal detection practice, only the component of the responsive field that oscillates at the frequency of excitation is used, to minimize the effect of background noise. However, unlike the standard practice, the location of the source of the responsive field is inferred from the response at a single location in space by measuring field gradients. Further, to increase detector sensitivity over standard metal detection techniques, the '986 Patent proposes the use of an improved magnetorestrictive sensor.

For detecting non-metallic medical objects, the '818 Patent proposes detecting the output of an RFID tag that has been attached to the medical object. Such tags are attached to medical objects by the manufacturer. The tags produce a coded output when stimulated by a time-varying electromagnetic field at the proper frequency. The output is a weak, narrow band signal that is modulated to identify a particular product/manufacturer combination.

As the '818 Patent explains, there is a problem obtaining sufficient signal strength from a small tag. However, increasing the size of the tag to provide greater signal strength is problematic for surgical sponges, which are asserted to be the most common medical object for which detection is important, because deformation of the sponge will often deform the tag, and using a large, non-deformable tag would defeat the purpose of the sponge.

The proposed solution to this problem is to increase the sensitivity of the detector so that it is capable of detecting the weak signals produced by small, inexpensive tags by stimulating the tag with a pulsed signal which covers a wide frequency range that includes the frequency of the tag. The pulsed signal triggers a continuing response signal from the tag, at its single frequency, which increases to a point where it becomes differentiated from background noise.

Both the '986 and the '818 Patents propose useful and desirable improvements to increasing detector sensitivity, for detecting the presence of and, to some extent, for locating the respective classes of medical objects within a body cavity in the operating room environment. However, the '986 patent does not recognize that the increased sensitivity of its detector will be accompanied by an increased sensitivity to noise, and that the standard practice of measuring only components of the responsive field that are synchronized to the frequency of excitation will not provide any additional noise reduction than has always been available in metal detectors, and which is known to be insufficient for this medical purpose.

Moreover, neither the '986 nor the '818 Patents recognize that the operating room is filled with other, similar medical objects, as well as many sources of general, broad-band electromagnetic radiation (such as CRT's), that are not located inside the patient but that are nevertheless nearby and will be detected. Many of the medical objects left behind inside a patient, such as needles and tagged sponges, will produce small signals or will only weakly interact with an interrogating field. Many of the external objects and sources will produce a stronger signal or other indication of presence, and neither patent provides any guidance for ensuring that what is detected is in fact of interest. Moreover, the improvements proposed in these patents are specific to sensing particular classes or types of objects; neither patent provides any guidance for improving the accuracy, precision, or specificity of detection and location in general, independent of what is being detected and the sensor technology being used.

Therefore, as the present inventor has recognized, there is a need for a method and apparatus for collecting data for detecting and locating disturbances that has particular applicability in the context of searching for medical objects, such method and apparatus also having wider applicability as discussed hereinbelow.

SUMMARY

A method and apparatus for collecting data for detecting and locating disturbances in space is disclosed. A plurality of distinct regions of the space are identified, and a device adapted for sensing positions of the device and respective representations of a field parameter at the positions is also disclosed. Preferably, the device comprises an inertial guidance system for determining the positions so that it can be hand-held and yet provide high accuracy and precision without requiring an articulated arm with position encoders.

According to a first, data collection aspect of the invention, the device is moved through the space to obtain a plurality of sets of the representations and corresponding positions. Positions falling within the regions are quantized, and, for each of the regions, the representations associated with the quantized positions therein are combined.

According to a second, presence testing aspect of the invention, the device is moved through the space in a first pass, to obtain first sets of the representations and the corresponding positions and thereby define baseline scan results. In addition, in a second pass distinct from the first pass, the device is moved through the space to obtain second sets of the representations and the corresponding positions and thereby define test scan results. The positions falling within the regions are quantized. For each of the regions having associated baseline scan results, the baseline scan results associated with the quantized positions therein are combined, defining combined, quantized baseline scan results, and for each of the regions having associated test scan results, the test scan results associated with the quantized positions therein are combined, defining combined, quantized test scan results. Respective representations of the difference between the combined, quantized test scan results and the combined, quantized baseline scan results are formed, defining ultimate data associated with said regions. Whether the ultimate data corresponding to at least one of the regions exceeds a threshold is evaluated.

According to a third, location determining aspect of the invention, the device is moved through the space to obtain a plurality of sets of the representations and corresponding positions. The positions falling within the regions are quantized. For each of the regions having associated scan results, the scan results associated with the quantized positions therein are combined, defining combined, quantized scan results. A first set of the combined, quantized scan results corresponding to at least two of the regions is identified. One or more possible locations of the disturbance in the space are triangulated using the first set.

Preferably further, the possible locations falling within the regions are quantized, defining quantized possible locations associated with the regions. For each of the regions having associated possible locations, the possible locations associated therewith are counted. One or more of the regions in which the location of the disturbance is most likely are identified by determining for which of the regions the counting produces a higher value than is produced for other regions.

It is to be understood that this summary is provided as a means of generally determining what follows in the drawings and detailed description and is not intended to limit the scope of the invention. Objects, features and advantages of the invention will be readily understood upon consideration of the following detailed description taken in conjunction with the accompanying drawings.

DETAILED DESCRIPTION OF PREFERRED EMBODIMENTS

Introduction

As mentioned above, the invention relates to a method and apparatus for collecting data, which may be used for detecting and locating disturbances. The term "disturbance" is used generally herein to refer to any matter or energy that is capable of being detected remotely. A source may create a disturbance in space by emitting into the space either energy, e.g., photons, or matter, e.g., gases. An object may disturb space by having material properties that interact with an applied field; for example, a ferrous metal object fixedly disposed within the magnetic field of the earth disturbs that magnetic field in the vicinity of the object. Particular embodiments disclosed herein pertain more particularly to such data collection for detecting and locating medical objects within the body cavity of a surgical patient; however, it should be understood that the invention may be used in any other desired data collection context without departing from its principles.

Sensing the presence of a medical object, concealed within a patient's body cavity, in the electromagnetically harsh environment of the operating room, presents unique and difficult challenges. Medical objects often provide only a weak signal, or otherwise only weakly interact with ambient or applied fields, so that their presence cannot easily be discerned over the electromagnetic noise that exists in the operating room. Further, as the size of medical patients varies considerably, the closest proximity that can be obtained by an external sensing device may be as high as 36 inches. Moreover, the body is primarily a saline solution, so that already weak electromagnetic signals emanating from either metal objects or RFID tags present within the body will be severely attenuated with distance. While the magnetic susceptibility of ferrous objects is useful for identifying ferrous objects, because the measurement is generally insensitive to the presence of salt water, many medical objects are non-ferrous, and some medical objects, such as needles, are quite small and will produce an exceedingly weak response. RFID tags also produce very weak signals, and are problematic for use on metal objects which are very common objects of interest.

It is also important in the medical application to discern the location of an object for which presence has been detected. While it is not so important to a hobbyist looking for buried artifacts, or an airport security screening device, to signal the precise location of an object that has been detected, the lack of having a precise location for a medical object in a patient's body cavity places a burden on the surgeon of searching the body cavity, which delays the completion of the surgery and adds to the risk of damage to the patient.

Accordingly, the present invention addresses a number of needs. Generally, the invention provides for improved (a) disturbance data collection, (b) disturbance presence detection, (c) disturbance location determination, and (d) disturbance location visualization. In addition, a novel and improved sensing device is disclosed for use in conjunction with disturbance data collection.

The various features of the invention are preferably used in combination with each other, but may be used in any desired combination and may be used separately. Moreover, the features of the present invention may advantageously be combined with additional features, such as those proposed in the '986 and '818 Patents discussed above. It should also be understood that sensing technologies depend on the disturbance being sensed. For example, for sensing chemical objects, an appropriate sensing device would be adapted for detecting the presence of a particular chemical by reacting with liquid or gas evolving from the object. It is generally intended that the methodologies described herein may be utilized in conjunction with any type of sensor or sensing technology appropriate to the disturbance being sensed.

Reference will now be made in detail to specific preferred embodiments of the invention, examples of which are illustrated in the accompanying drawings. Wherever possible, the same reference numbers are used in the drawings and the description to refer to the same or like parts.

Device Description

Figure 1:
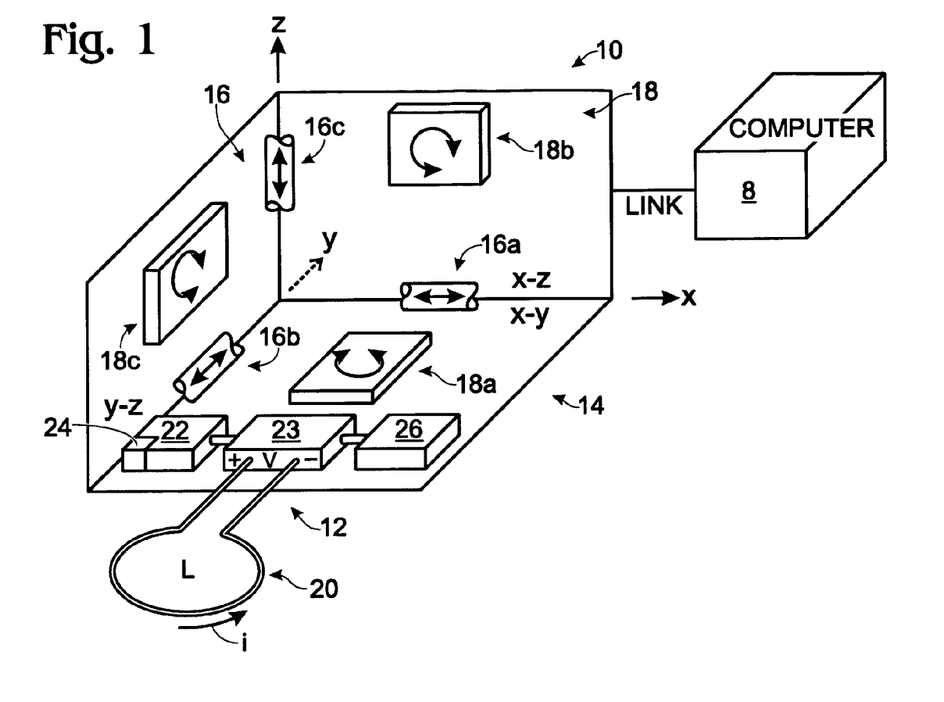
FIG. 1 is a schematic perspective illustration of a hand-held sensing device for use according to the present invention.

FIG. 1 shows a hand-held device 10 for use according to the present invention. As will be explained in more detail below, the device measures a field parameter, such as magnetic permeability, at different points in a space as the device is moved through the space by hand. For example, as shown in FIG. 2, the device 10 may be moved about in a space 11 by hand, represented by paths "A" and "B." While the paths "A" and "B" are shown in two-dimensions, it will be understood that the space may be, and typically is, three-dimensional, so that the paths may represent a course of travel anywhere within a three-dimensional space.

Figure 2:
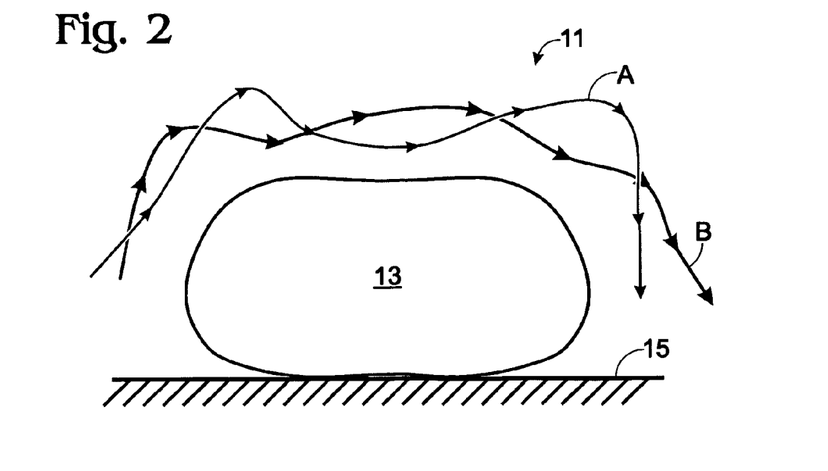
FIG. 2 is a cross-sectional view of a surgical patient showing movement of the hand-held device of FIG. 1 in a space around the surgical patient according to the present invention.

Also shown in FIG. 2 is an idealized cross-section of a patient 13 lying on a table 15. The patient may be a human being or any other animal. In a preferred method according to the invention, the device 10 is moved in space surrounding the patient to obtain measurements of a field parameter useful for determining (a) whether a medical object is present inside the patient, and (b) if so, what the location of the medical object is. The medical object is typically either a metal object, such as a clamp or a needle, or a non-metallic object, such as a sponge to which is attached an RFID tag. However, it will be understood that the principles described herein may be applied to numerous other situations and circumstances in which it is desired to determine the presence of disturbances, or to discern the location of any such disturbances that are present.

Returning to FIG. 1, the device 10 includes a position sensing portion 14 adapted to measure the position of the device in space. It is desired to provide as much precision and accuracy in the sensed position as is possible or practical, but there is no requirement that the precision and accuracy of the disturbance sensing portion 12 exceed any particular threshold.

As has been provided in the art of medical imaging before, the position sensing portion 14 preferably includes three accelerometers 16, namely 16a, 16b, and 16c, all arranged to respond to accelerations directed along different axes, preferably orthogonal axes such as the x, y, and z Cartesian axes shown. As is well known, the x, y, and z position of the device at any instant can be obtained by double integration of the outputs of the respective accelerometers, assuming that the orientation of the device is maintained as it is moved about. However, since the device 10 is hand-held and is moved through space by hand, the orientation of the device will generally not be maintained fixedly in space. Therefore, the outputs of the accelerometers must be corrected for changes in orientation, requiring measurements of orientation corresponding to the measured positions.

To provide measurements of orientation, three gyroscopes 18, namely,18a, 18b, and 18c, are provided to respond to changes in angle of the device 10 along different axes, preferably the same axes used for measuring acceleration. For example, with reference to the coordinate system defined by the axes x, y, and z, the gyroscope 18a is sensitive to changes in angle within the x-y plane (commonly referred to as "yaw"), the gyroscope 18b is sensitive to changes in angle within the x-z plane (commonly referred to as "roll"), and the gyroscope 18c is sensitive to changes in angle within the y-z plane (commonly referred to as "pitch").

The gyroscopes 18 provide as outputs changes in angle that can be used to correct the outputs of the accelerometers by the use of trigonometry. For example, consider that an accelerometer, e.g., 16a, sensitive to accelerations along the "x" axis, measures an acceleration. Further consider that no acceleration is measured by an accelerometer, e.g., 16b, sensitive to accelerations along the "y" axis. However, consider that a gyroscope 18a, sensitive to changes in angle within the "x-y" plane, measures that the angle of the device 10 within this plane has deviated 45 degrees away from the "x" axis toward the "y" axis. In that case, the acceleration measured on the "x" axis is actually the acceleration along a line oriented at 45 degrees with respect to the "x" axis. The acceleration along the "x" axis corrected for this change in angle is obtained by multiplying the measured acceleration by the cosine of 45 degrees. Similarly, the acceleration along the "y" axis corrected for this change in angle is obtained by multiplying the measured acceleration by the sine of 45 degrees.

The principles of operation of such position sensing mechanisms are well known, so that further discussion is omitted as not being particularly pertinent to the invention. However, it may be noted in passing that such mechanisms, including accelerometers and gyroscopes, are now being included in standard integrated circuits, and such integrated circuits are preferable for use in a hand-held device because it reduces weight, power consumption and cost.

For purposes of convenience, but not of limitation, a position sensing mechanism that determines position by use of accelerometers and gyroscopes will be referred to herein as an "IGS" system (acronym for inertial guidance system). The IGS provides the particular advantage that positions can be determined in a hand-held device and yet provide high accuracy and precision without requiring an articulated arm. By contrast, position sensing using a GPS (acronym for global positioning system) does not provide the required precision, and articulated arms providing for more precise and accurate position sensing using position encoders at the joints will interfere with the lines and wires commonly surrounding a surgical patient.

Referring again to FIG. 1, the device 10 further includes a disturbance sensing portion 12 for sensing a field parameter indicative of the presence and magnitude of a disturbance within the measurement space.

Exemplary field parameters for use in sensing the presence and properties (e.g., size) of metal objects are magnetic permeability and electrical conductivity. Particularly, metal objects perturb both magnetic and electric fields. Metal objects perturb electric fields because their conductivity attracts and therefore increases the density of electric field lines existing in an otherwise non-conductive space, e.g., a space filled with air. Similarly, magnetically permeable metal objects perturb magnetic fields because their magnetic permeability attracts and therefore increases the density of magnetic field lines existing in an otherwise non-magnetically permeable space. It is a recognition of the present inventor that magnetic fields, unlike electric fields and electromagnetic waves or signals, are unaffected by saline cavities such as are present in animals. Thus, the magnetic field parameter is a preferred field parameter according to the present invention for collecting data regarding metal objects.

It is desired to provide as much precision and accuracy in sensing the presence and magnitude of a disturbance as is possible or practical. However, as will be explained hereafter, methods according to the invention improve on the raw precision and accuracy provided by the disturbance sensing portion 12, so it is not necessarily critical that the precision and accuracy of the disturbance sensing portion 12 exceed any particular threshold.

FIG. 1 shows a loop sensor 20 of the disturbance sensing portion 12 for sensing magnetic permeability. The sensing is based on the principle that the inductance of the loop sensor is responsive to the presence of nearby metal objects. For general purposes, the inductance of the loop sensor may be monitored by a control circuit 23 through use of the known relationship between the voltage across an inductor and the current therein, V=L di/dt.

Figure 3A:
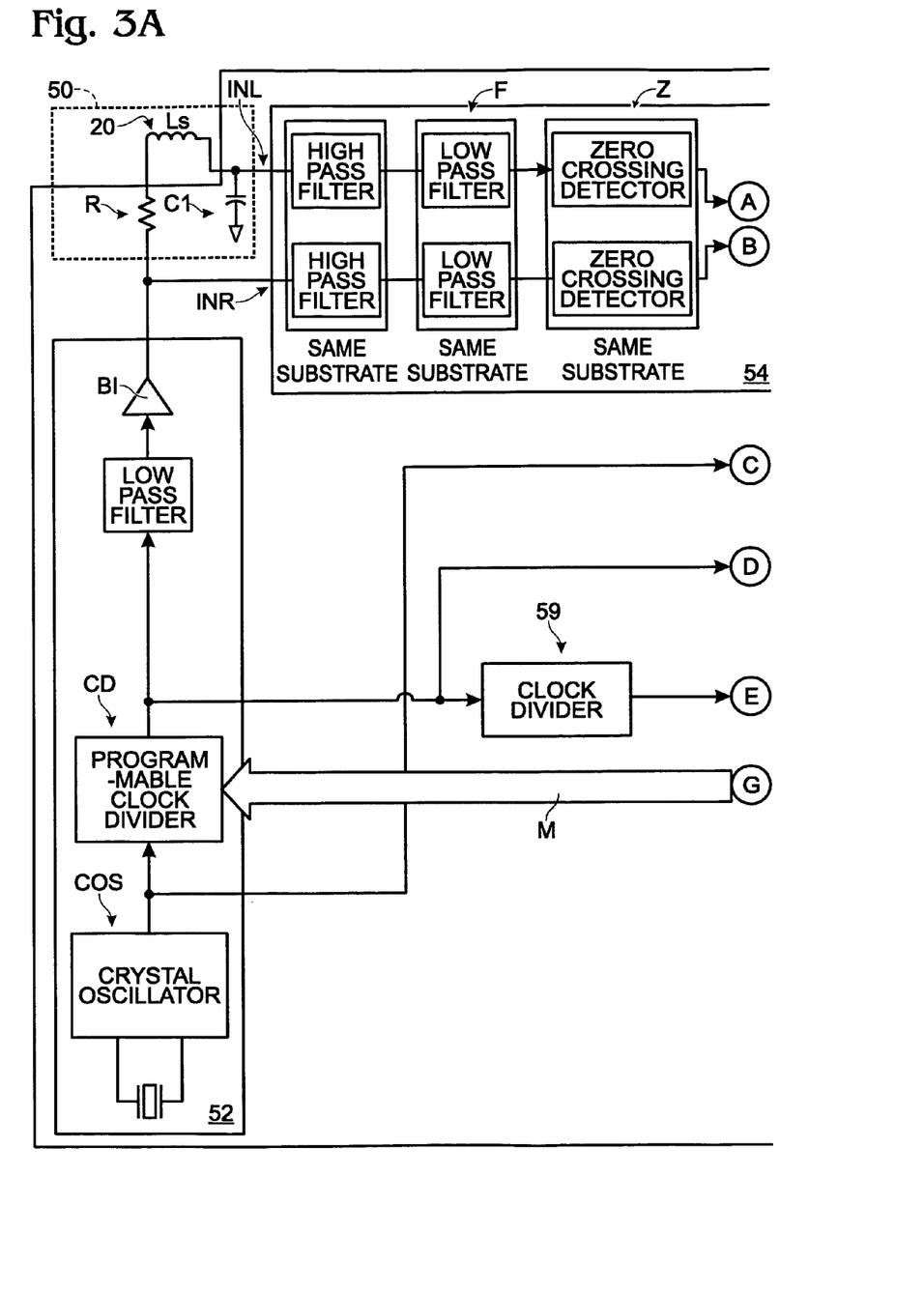
FIG. 3 is a block diagram of a loop sensor and a portion of a control circuit for controlling the loop sensor for sensing changes in permeability to very high stability and sensitivity according to the present invention.
Figure 3B:
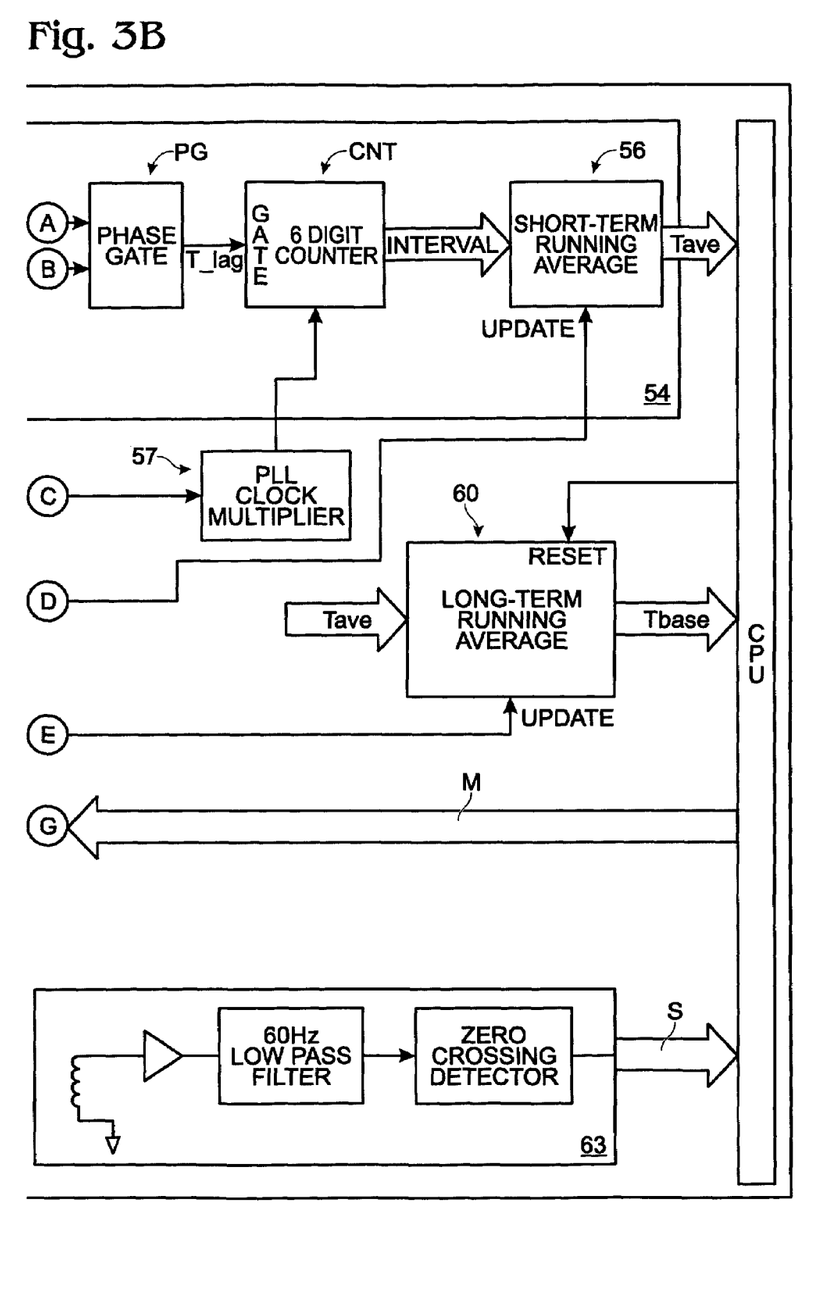

However, unusually high stability and sensitivity in sensor measurements are needed to discern reliably the presence of, and locate, medical objects in the bodies of medical patients in the operating room. FIG. 3 shows a block diagram of the loop sensor 20 along with a pertinent portion of a novel control circuit 23 that is particularly adapted for meeting these needs. Through these means, the device 10 provides for tracking extremely small changes in the inductance of a coil of wire by utilizing matched delay paths and a high-speed time sampling circuit to compare the phase shift between voltage and current while the coil is being driven at its resonant frequency.

The device 10 senses changes in permeability as a result of changes in the effective inductance of the loop sensor 20, due to a variable proximity of the loop sensor to metal objects. To provide for high sensitivity, a resonant circuit 50 is formed from the loop sensor 20, a capacitor C1, and a resistor R. The resonance circuit is maintained at a fixed resonant frequency $F_0$ that is the actual resonance frequency of the circuit 50. Changes in inductance of the loop sensor 20 are sensed as a phase differential. At resonance, the phase differential is zero, but on either side of resonance, the phase differential changes dramatically between being positive (at +90 degrees) and being negative (at −90 degrees).

The actual resonance frequency $F_0$ is generally unknown because it can vary within about 10-15% of an ideal, calculated value based on circuit parameters. The circuit is controlled to operate at resonance, however, by use of a "feedback control cycle" initiated by the CPU wherein the CPU monitors the phase differential to determine when the phase differential passes through resonance, and tunes a programmable oscillator 52 via a signal "M" to drive the circuit 50 at the frequency $F_0$. Once a convergence on the actual resonant frequency $F_0$ is determined, the feedback control cycle is discontinued and the driving frequency remains fixed until a new feedback control cycle is initiated as indicated below.

The phase differential is determined by comparing the phase of the voltage output of the circuit 50 and the phase of the voltage output of the programmable oscillator 52. These phases are input to a phase shift monitoring circuit 54 at inputs INL and INR thereof, respectively.

A low noise, low output-impedance buffer B1 is used to interface the oscillator 52 to the resonant circuit 50. The frequency of the oscillator 52 may be programmed by adjusting a programmable clock divider CD operating on the output of a crystal oscillator COS.

The phase shift monitoring circuit 54 receives the signals input at INL and INR in parallel, and passes these parallel inputs through twin, matched paths comprising matched filters F and matched zero crossing detectors Z, each matched pair being provided on the same chip substrate to cancel out phase differential between the paths due to inequality of device parameters due to manufacturing variations. Matched delay paths are provided by utilizing matched, common substrate semiconductor devices for both analog and digital circuit elements in the circuit 23.

A phase gate PG receives the outputs of the zero crossing detectors and outputs a signal T_lag which specifies the differential in phase between the two paths. T_lag is used to start and stop a counter that counts at very high frequency compared to the frequency $F_o$, as controlled by a clock multiplier 57 that is phase locked to the oscillator 52, to obtain a digital signal, "Interval," representing an interval of phase differential which is a high precision fraction of $F_o$, preferably on the order of 1:100,000 or better.

The production of the signal "Interval" is repeated at times defined by the base frequency of the oscillator 52 to produce samples of "Interval" at a frequency on the order of 1000 samples/second. These samples are provided to a functional block 56 that forms a short term running average of the samples. This averaging is performed over a short period of time, providing a response time on the order of 100 times a second, to essentially low-pass filter or smooth the samples to produce measurement data, "Tave."

A functional block 60 produces long term running average signals, "Tbase," based on averages of the short term running average taken over long periods of time defined by the base oscillator 52 as modified by another clock divider 59, extending on the order of one second.

As mentioned above, the circuit 50 is controlled to operate at resonance by use of a CPU that monitors the phase differential to determine when the phase differential passes through resonance, and tunes a programmable oscillator 52 to drive the circuit 50 at the frequency $F_0$. To monitor the phase differential for implementing this control, the CPU uses Tbase to ensure that discerned resonant frequency is not affected by variations due to changing proximities to metal objects that are the subject of search, as these variations will average out over long times.

The signals Tbase are preferably accumulated by the CPU, which resets the block 60, and are averaged over even longer times, e.g., on the order of hours or days, to provide a reference signal Tref (not shown) that averages out variations, such as those due to changes in temperature, that occur over very long times. Tref is subtracted from all of the measurement data Tave to provide ultimate measurement data for which all reasonable environmental and circuit parameter variations have been compensated for. Tref is also used to provide a starting or seed value of the programmable clock divider CD used in a feedback control cycle to facilitate fast convergence to the resonant frequency $F_0$ when the device 10 is first turned on.

The frequency of the resonant circuit is preferably chosen to be high enough to prevent interference with ECG measurements and to facilitate blocking 60 Hz noise, but still low enough that the high frequency counter CNT can be implemented using standard integrated circuit technology. As this technology is always improving, it is expected that the upper bound of the resonant frequency can be increased over time.

Magnetic field effects due to local 60 Hz noise produce a bimodal distribution of phase differential due to the sampling frequency being much higher than 60 Hz. An algorithm within the CPU cancels out the bimodal distribution and extracts a valid center value of the measured delay. In order to enhance the accuracy of this extraction process, the CPU is supplied with an ambient 60 Hz zero-crossing disturbance signal "S" produced by a functional block 63.

An exemplary field parameter for collecting data regarding RFID tags is electric field strength, which in particular is discerned as an electric signal emanating from the RFID tag. For this purpose, an antenna optimized for the frequency of the signal transmitted from the RFID tag is used in place of or in addition to the loop sensor 20.

The device 10 still further includes a sampling portion 22 having a clock 24. The sampling portion 22 outputs a signal in response to the clock 24 that instructs the sensing portion 12 to make a measurement and store the measurement in a memory 26. The clock 24 is also used to instruct the position sensing portion 14 to register the sensor's coordinates at the sample time. It is not essential that the clock 24 output a regular clock signal at a single frequency; however, at least a real-time clock base is preferably provided to ensure that samples are in fact taken throughout the entire space in which the hand-held device 10 is moved.

Data Collection Methodology

The device 10 is enabled by the aforedescribed adaptations to collect data in space. The data represent the magnitude of a selected field parameter and are associated with a given location or position within the space. As the device 10 is hand-held and hand-carried, the positions in space at which the data are collected are variable and unpredictable. However, the methods and apparatus described herein overcome this problem.

Figure 4:
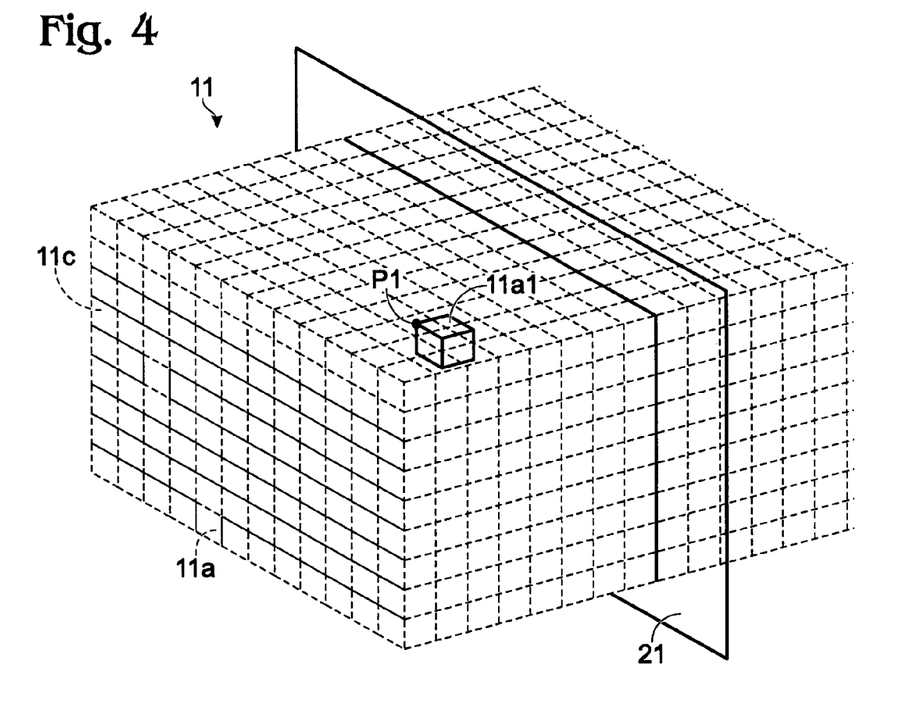
FIG. 4 is a pictorial view of a space partitioned into cellular regions according to the present invention and also showing a slice of the space lying in the plane of FIG. 2.

Turning to FIG. 4, the space 11 is shown partitioned into three-dimensional cellular regions or regions 11a. The cellular regions 11a are distinct regions of the space. Preferably, for computational ease, the cellular regions are defined so as to form a regular, orthonormal lattice structure as shown, but this is not essential.

Figure 5:
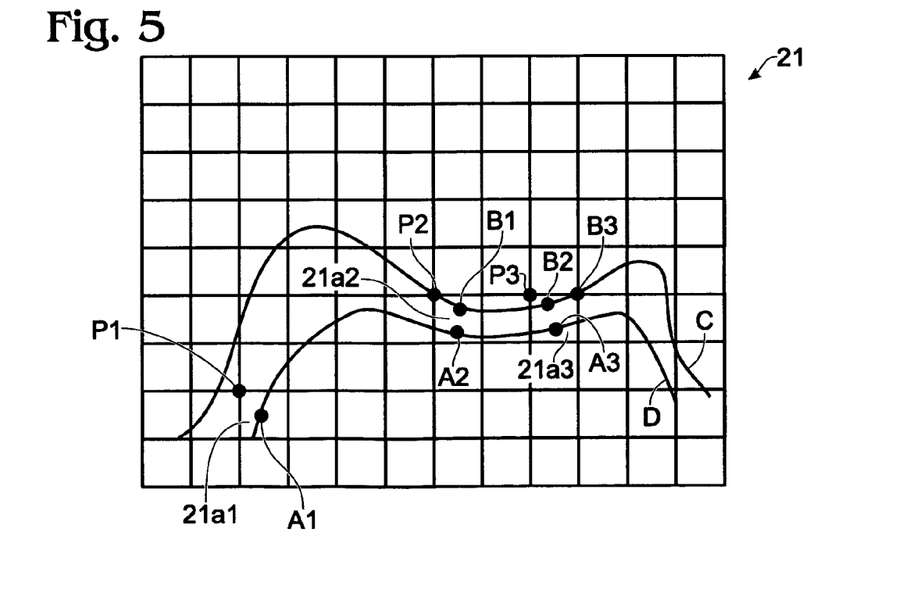
FIG. 5 is a pictorial view of the slice of FIG. 4 partitioned into cellular areas that correspond to a sub-set of the cellular regions of FIG. 4 according to the present invention.

FIG. 5 shows a two-dimensional "slice" 21 of the space 11 shown in FIG. 4. The slice 21 is preferably taken laterally with respect to the patient 13 in FIG. 2, i.e., in the plan of the Figure, though this is not essential. A path "C" represents the path of the device 10 as it is carried through the space 11. While the path "C" is shown lying entirely on the slice 21 for illustrative purposes, it should be understood that, in practice, the path "C" would travel through the three-dimensional space 11. The path "C" therefore represents a "pass" through the space 11.

As the device 10 is moved along the path "C", the sampling portion 22 causes samples of the field parameter to be taken, i.e., data "A1," "A2," ... "A12." These data have associated positions as indicated in FIG. 5 by the placement of the data along the path. The spacing between the positions appears randomized due to the fact that the device, which because it is moved by hand, is not moved at a constant velocity.

The slice 21 is partitioned into cellular areas 21a that correspond to the three-dimensional cellular regions 11a of the space 11 (FIG. 4). Particularly, the cellular areas 21a may represent faces of the cellular regions 11a lying on the x-y axes.

A second path "D" is also shown representing a second pass through the space. As the device 10 is moved by hand, the second path "D" is not coincident with the path "C," and samples of the field parameter are taken at different positions, resulting in data "B1," "B2," ... "B10."

According to the invention, all of the aforementioned data are spatially averaged by "quantizing" the positions of the data. As used herein, "quantizing" the positions of data means that all of the data taken within a given cellular region, which is used as a fundamental unit of a measurement space, are associated with and assigned to a single point or position in the measurement space.

In the two dimensions shown in FIG. 5, the positions are quantized within the corresponding cellular areas 21a. For example, the position of the datum "A1" is quantized to a point "P1" corresponding to the cellular area 21a1 (and the cellular region 11a1 of FIG. 4). The positions of the data "A2" and "B1" both fall within the cellular area 21a2 and both are assigned a quantized location "P2" corresponding to the cellular area 21a2. The positions of the data "A3," "B2," and "B3" each fall within the cellular area 21a4 and are all assigned the quantized location "P3." It should be understood that the selection of the quantization points within the cellular areas and cellular regions is arbitrary; however, it is preferable to choose points that are, like the cellular areas and cellular regions, also regularly spaced from one another.

It should be understood and emphasized that, while quantization within a slice is shown and described for illustrative convenience, in general, quantization is performed for data positions falling anywhere within the corresponding cellular region 11a shown in FIG. 4. That is, each cellular region 11a has an associated point "P" at which data positions falling within that region are quantized. The data associated with paths "C" and "D" as described above may therefore be viewed as those data associated with the paths "C" and "D" falling on the slice 21, so that there are other data having positions falling at other locations within the space 11a off the slice 21 that are not being shown in FIG. 5.

In addition to spatially averaging the data positions, the data themselves are averaged or otherwise combined. Particularly, data associated with a given quantized data position are combined where, preferably, the combination is a simple average. For example, the data "A2" and "B1," which are each assigned the quantized position "P2," are averaged together. A simple such average would sum the data "A2" and the data "B1" and divide the result by two. Similarly, the data "A3," "B2," and "B3" assigned the quantized position "P3" are averaged together.

RFID tag data present a special case that is discussed below in connection with presence detection and location determination.

As the data are acquired at randomized locations in the space 11, some cellular regions 11a will have no data associated therewith, some cellular regions may have only a single datum associated therewith, and other cellular regions may have a number of data associated therewith. Preferably, cellular regions for which no data are associated therewith are identified and discarded in any subsequent analysis. For convenience, hereinafter, it is assumed that references to cellular regions for purposes of analysis as described are cellular regions for which data are associated therewith.

According to the data collection methodology, discrete data that are originally gathered at randomized positions within the space 11 are transformed to combined or averaged data corresponding to specific, fixed positions in the space 11. The data thus transformed and thereby collected may be used according to the invention for (a) detecting the presence of a disturbance, or (b) locating the disturbance in the space 11.

It is important to appreciate that the data collection methodology provides for high sensitivity in the data by providing a novel framework for combining data. Here, "high sensitivity" in the data is distinguished from the high sensitivity of the sensor, which is due to the very high gain in the sensor's circuits and which makes the sensor highly sensitive to noise. The sensor's high sensitivity to noise is compensated for according to the invention to produce high sensitivity in the data to signal by making a large number of passes of the device through the space, tolerating the randomness in the positions of acquired data caused by moving the device by hand through the use of spatial averaging, and accumulating a large number of data to be used in a data averaging which both reduces noise and increases signal. This novel data collection methodology thereby provides an unusual capability to "see" weak disturbances. Even in cases where the sensor's sensitivity is not or does not need to be exceptionally high, these techniques allow a hand-held device to detect reliably relatively weak disturbances within a very noisy environment.

Presence Detection

Presence detection according to the present invention may be performed for both coded and non-coded disturbances. A coded disturbance is a disturbance having a specific, known signature, such as the transmission of a code from an RFID tag. A non-coded disturbance is a disturbance for which a field parameter is measured as a random variable.

Non-Coded Disturbances

For non-coded disturbances, the field for which a parameter is measured by the sensing portion 12 may be generated specially for detection purposes, but the invention contemplates collecting data, using as many passes of the device 10 through and about the space 11 as is desired to obtain a desired level of sensitivity in the presence of an ambient or pre-existing field. According to the data collection methodology, quantized data positions and combined data are associated with the cellular regions 11a, characterizing the space 11 under ambient conditions. This characterization may be performed, for example, in an operating room with the patient present but before surgical procedures are commenced on the patient. All of the passes associated with a completed characterization is termed herein a "scan," and a scan under ambient conditions is termed herein a "baseline scan."

Figure 6:
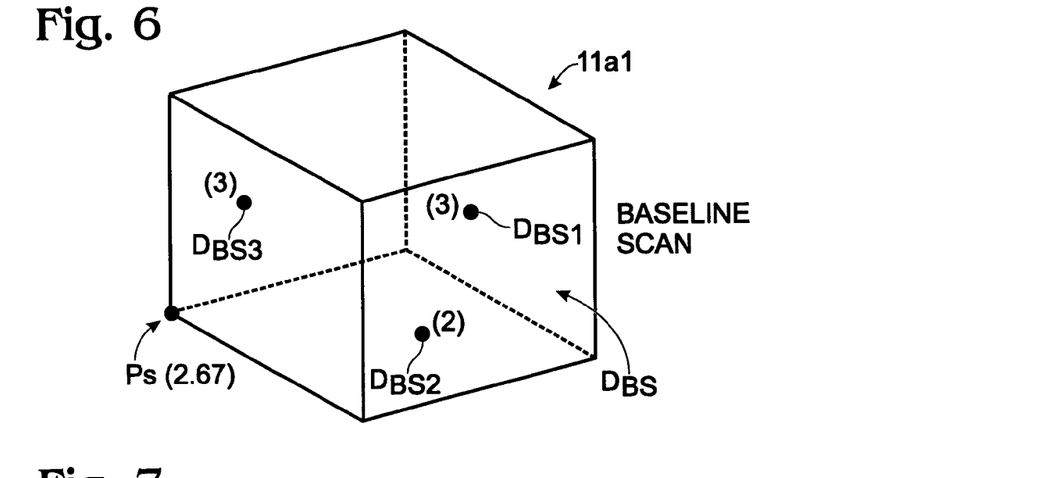
FIG. 6 is a pictorial illustration of a cell region, illustrating data corresponding to a baseline scan according to the present invention.

However, as surgery is being completed, it is now desired to detect the presence of any medical objects unintentionally left behind inside the patient. According to the invention, the space is re-characterized in a second, "detection scan" using the device 10 in the same manner as before to determine whether there are any significant changes in field parameters. For example, with reference to FIGS. 6 and 7, there is assumed to be a cellular region 11a1 through which the device 10 has been separately passed in a BASELINE SCAN, and in a DETECTION SCAN, respectively. In the exemplary BASELINE SCAN as shown in FIG. 6, three data points $D_{BS}$ happen to have been obtained, namely $D_{BS1}$, $D_{BS2}$, and $D_{BS3}$. Each of the three data points $D_B$ have associated therewith a measured value (indicated in parentheses in the Figures), e.g., the value of the data point $D_{BS1}$ may be assumed to be 3, the value of the data point $D_{BS2}$ may be assumed to be 2, and the value of the data point $D_{BS3}$ may be assumed to be 3. These data are quantized so as to be associated with a single quantization point $P_S$ associated with the region, and combined (here averaged) so that, along with the point $P_S$, there is associated a number $(3+2+3)/3=2.67$.

Figure 7:
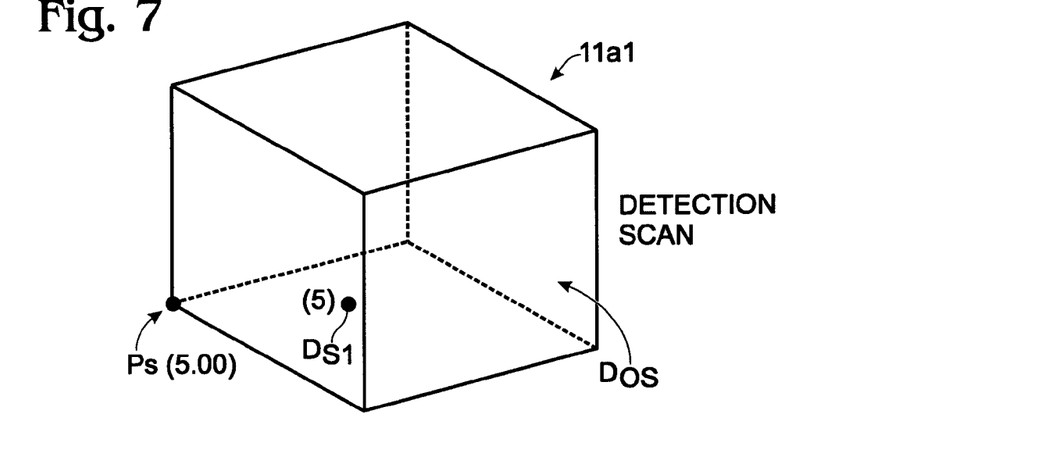
FIG. 7 is a pictorial illustration of the cell region of FIG. 6, illustrating data corresponding to a detection scan according to the present invention.

In the exemplary DETECTION SCAN as shown in FIG. 7, only one data point $D_{DS}$ happens to have been obtained, namely $D_{DS1}$. Supposing that a disturbance that was not present during the BASELINE SCAN has occurred and is sensed by the device 10 during the DETECTION SCAN, the value of the data point $D_{DS1}$ may be assumed to be a relatively large value, e.g., 5. Since there is only one data point in the DETECTION SCAN, the average associated with the quantization point $P_S$ of the data in this example is 5.00

Figure 8:
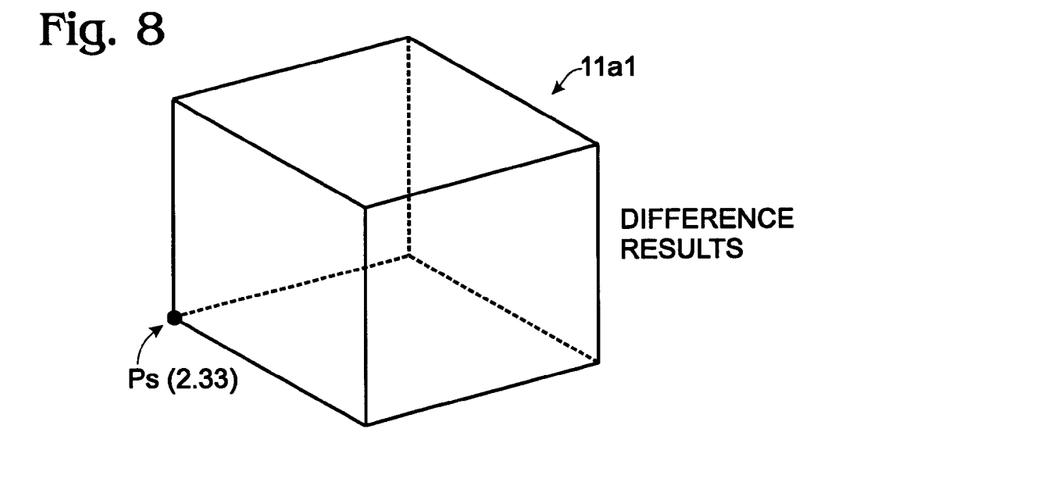
FIG. 8 is a pictorial illustration of the cell region of FIG. 6, illustrating data corresponding to difference results according to the present invention.

Finally, with reference to FIG. 8, a difference operation ("DIFFERENCE RESULTS") is performed between the combined data of the BASELINE SCAN and the combined data of the DETECTION SCAN. In the simplest example, the difference result is the arithmetic difference between the value associated with the region 11a1 for the BASELINE SCAN, i.e., 2.67 in this example, and the value associated with the same region for the DETECTION SCAN, i.e., 5.00, this difference being 2.33 as indicated at the quantization point $P_S$.

The difference results may be analyzed in a number of ways to decide whether a disturbance is present. As one example, a disturbance can be detected if the difference results for one cellular region, irrespective of the difference results for other regions, exceeds an absolute threshold. As another example, the difference results for one cellular region can be compared to an average of the difference results for a number of other cellular regions which can be used to establish a noise floor. As still another example, difference results for a cellular region that fail to exceed the absolute threshold of the first example above may nevertheless be considered to indicate the presence of a disturbance if, in combination with exceeding a decreased threshold, the difference results for adjacent or nearby cellular regions also exceed a threshold.

Coded Disturbances

Coded data have both a binary aspect and a magnitude aspect. That is, such a disturbance produces data that can be considered to be either valid or invalid, and the signal that carries the data has a magnitude or strength that diminishes with distance from the signal source. The magnitude aspect of coded disturbance data may and preferably is collected and used in the same manner as the non-coded disturbance data discussed immediately above. Further, the magnitude aspect is used for location determination as described in the section below. However, a presence indication for a coded disturbance determined in this manner may be corroborated using the binary aspect by identifying the disturbance to confirm the indication, and therefore to further enhance the accuracy of the method.

An exemplary and preferred coded disturbance for the medical purposes discussed herein is an RFID tag. In the binary aspect of RFID tag data, the correct code for the tag is either present or not. For example, no code may be received, a partial or unintelligible code may be received, or a code may be received that does not conform to a known or expected code corresponding to an object for which the search is being directed. For example, a sponge used in surgery may be tagged with an RFID tag, but other objects or devices in the operating room might also be tagged. The surgeon is interested only in the presence of the sponge, and so the method is looking for a unique code.

Such binary aspects of the data may be combined or averaged by counting the number of incidences of valid data. For example, within a particular cellular region, samples indicating that a proper code is present may be counted to obtain a total presence count. While instances of invalid data are ordinarily not counted, such instances may be counted and subtracted from the presence count if desired.

As for the difference results for non-coded disturbances, the presence counts may be analyzed in a number of ways to decide whether a disturbance is present. As one example, a disturbance can be detected if the result of the presence count for one cellular region, irrespective of results for other regions, exceeds an absolute threshold. As another example, the presence count for one cellular region can be compared to an average of the presence counts for a number of other cellular regions which can be used to establish a noise floor. As still another example, a presence count for a cellular region that fails to exceed the absolute threshold of the first example above may nevertheless be considered to indicate the presence of a disturbance if, in combination with exceeding a decreased threshold, the presence counts for adjacent or nearby cellular regions also exceed a threshold.

Location Determination

For non-coded disturbances, locating a disturbance may be accomplished according to the invention by using the detection scan results as points for triangulating the disturbance. The same is true for coded disturbances, using the aforementioned magnitude aspect of coded disturbance data. For example, the magnitude aspects of RFID tag data may be treated as any other data associated with a random variable or field parameter. That is, the strength of the signal conveying the code of an RFID tag has a range of possible values, and combining or averaging the data is accomplished in the ordinary manner for location determination as described below.

In addition to refining the data according to the novel methodology discussed above, preferably, though not necessarily, a triangulation is performed according to the invention in two other distinct ways: (1) data points used in a given triangulation are those lying on a single slice; and (2) an indeterminate data set is used for triangulation to generate, instead of a point location of the disturbance, a locus of points that are possible locations of the disturbance. The number of loci passing through a given cellular region is counted and those cellular regions containing the most loci are determined to be most likely locations of the disturbance.

It should be understood, however, that triangulation generally contemplates any methodology by which data associated with a plurality of points that are spaced apart from one another and that are responsive to a disturbance are used to infer the location of the disturbance.

Triangulation of a disturbance depends on having data about the disturbance that are representative of distance from the disturbance. For fields such as electric fields, field strength falls inversely with the square of the distance from the disturbance. For other disturbances, the measured field parameter may have some other relationship to distance. For some disturbances, the actual distance may be determined from the measured field parameter, but in general, only relative distances can be determined. For example, if a field strength is measured as "five units" at a first location and "ten units" at a second location, and it is known that the magnitude of the measured parameter falls off inversely proportional to the square of the distance from the disturbance, then all that can be determined from these two measurements it that the first location is four times farther away from the disturbance than the second location. By contrast, if it is known how strong the disturbance is, each measurement by itself would be sufficient to determine distance from the disturbance.

Figure 9:
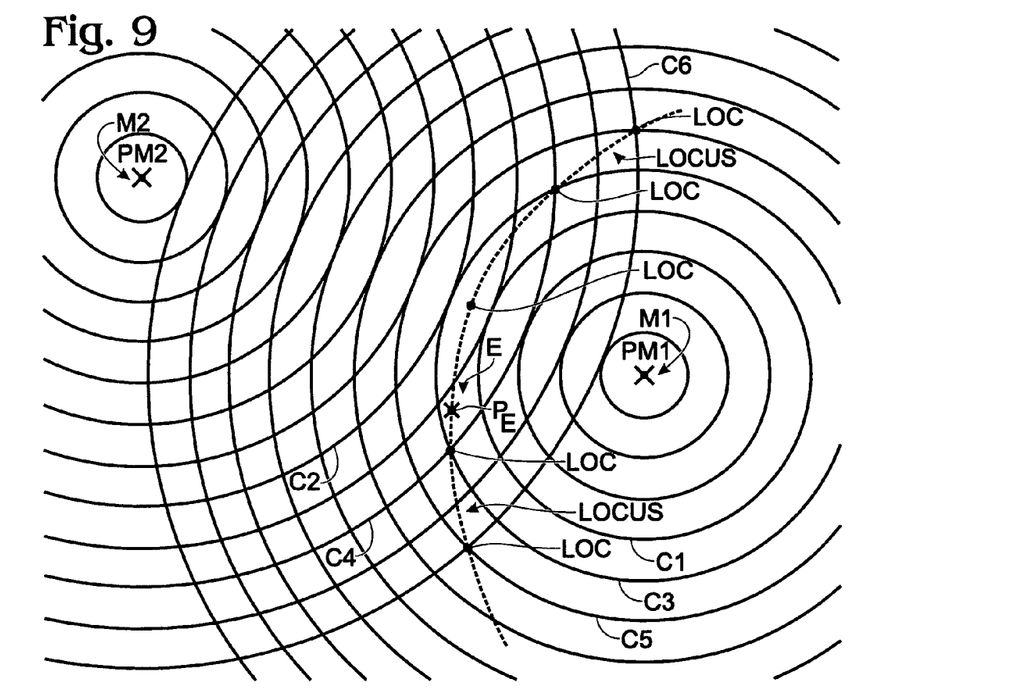
FIG. 9 is a graphical illustration of the construction of a locus of points according to the present invention.

In general, it is recognized herein that two points lying in a plane and spaced apart from one another provide a locus of points through triangulation that could correspond to the location of the disturbance. FIG. 9 illustrates the principle. Assume a measurement M1 is taken at a point $P_{M1}$ and a measurement M2 is taken at a point $P_{M2}$ of a disturbance "E" that is located at a point $P_E$.

A number of concentric circles can be drawn around the points $P_{M1}$ and $P_{M2}$ respectively. Each circle, by its radius, represents a possible value of the measured field parameter caused by the disturbance E were it located on that circle. For example, a circle C1 about the point $P_{M1}$ having a radius R1 represents a first possible value of M1 if the disturbance E lies on the circle C1. A concentric circle C2 having a second radius R2 represents a second possible value of M1 corresponding to the disturbance E lying on the circle C2. Where R2 is twice R1, for an inverse square relationship to distance, values of M1 corresponding to the disturbance being somewhere on the circle C1 would be expected to be four times higher than values of M1 corresponding to the disturbance being on the circle C2.

Applying a similar set of circles about the point $P_{M2}$ there is the same relationship between the radii of these circles. Moreover, there is the same relationship between the radius of circles centered on the point $P_{M1}$ and the radius of circles centered on the point $P_{M2}$.

Possible locations of the disturbance are identified as points where circles centered on the point $P_{M1}$ cross circles centered on the point $P_{M2}$. Assume that the value of M1 is four times the value of M2 and that there is an inverse square relationship to distance. Thence, each circle centered on the point $P_{M1}$ is related to a corresponding circle centered on the point $P_{M2}$ in that the radius of the circle centered on the point $P_{M2}$ is twice the radius of the corresponding circle centered on the point $P_{M1}$. For example, circles C1, C3, and C5 centered on the point $P_{M1}$ correspond respectively to circles C2, C4 and C6 centered on the point $P_{M2}$. More particularly, the radius of the circle C2 is twice the radius of the corresponding circle C1; the radius of the circle C4 is twice the radius of the corresponding circle C3; and the radius of the circle C6 is twice the radius of the corresponding circle C5. Where corresponding circles cross, a continuous locus ("LOCUS") of points ("LOC") is defined. Points lying on the locus are all the possible locations of the disturbance E according to the measurements M1 and M2.

The lack of determinance of the location of the disturbance, i.e., the lack of being able to locate the disturbance "E" at the point $P_E$, flows from the fact that only two points were used in the triangulation. If a third point were used, then the locus would collapse to a single point that is within an error bound of the point $P_E$. To locate the point $P_E$ with greater accuracy, a number of sets of three measurement points would be used to develop a scatter plot of possible locations of the point $P_E$ that would, assuming that the measurements exhibited only random error, converge on the point $P_E$. In addition to showing convergence, the method provides an indication of the error, as the density (or standard deviation) of the results will fall off with increasing distance from the median or convergence point $P_E$. Further, the method works equally well to discern convergence at multiple points, corresponding to multiple disturbances.

It has been discovered by the present inventor through computer simulations that using an indeterminate set of points to obtain a corresponding locus in combination with the methodology described below provides less noisy results than triangulating with determinate sets of the data.

As a brief review, data points for use in triangulation according to the invention are quantized spatially, and data corresponding to locations within a given quantization space are combined. For purposes of locating one or more disturbances according to the invention, difference results are next obtained on a cell-by-cell basis. The difference results reflect, for each cellular region, changes in the measured field parameter within that region detected in the detection scan with respect to the baseline scan.

Next, the difference results themselves are combined for triangulation in the manner described above. Particularly and preferably, various combinations of sets of two difference results, each set of two difference results corresponding to two different cellular regions 11a, are used to generate corresponding loci. The loci are curvilinear lines passing through specific cellular regions 11a. According to the invention, a histogram is developed for each cell region reflecting the number of counts that a locus passes through the region. Cellular regions 11a having higher counts are cellular regions in which the location of a disturbance is more likely. Assuming that the difference results exhibit only random error, the cellular region having the highest count will be the most likely location of the disturbance, and the decrease in likelihood exhibited by nearby cellular regions having lesser counts provides an indication of the error.

Graphical Visualization

Often, as in the case of locating medical objects in medical patients, the location of a disturbance is determined for the purpose of retrieving the object. According to the invention, the positions already obtained by the device 10 can be of use for this purpose. Particularly, the passes of the hand-held device 10 through the space 11 describe curvilinear lines in the space that may be used to define a three-dimensional surface. The three-dimensional surface can be displayed on a graphics display device, along with a determined location (or locations), the surface providing a useful reference against which the location can be visualized.

Figure 10:
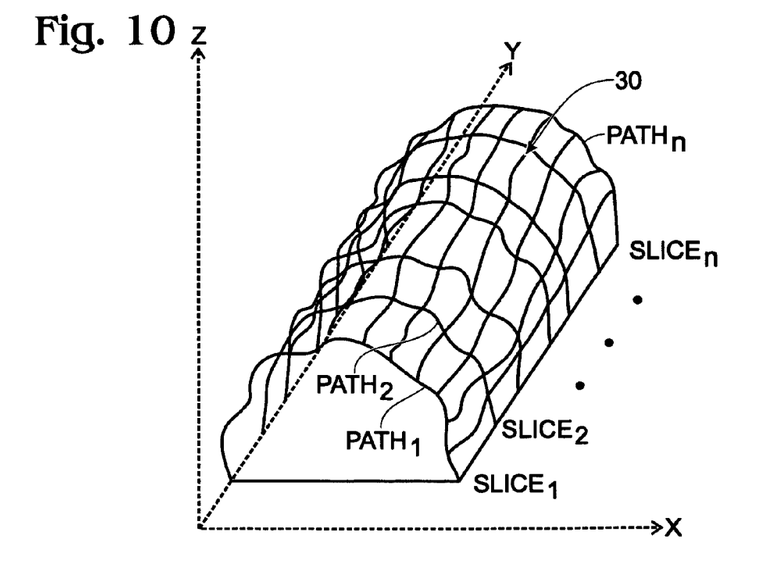
FIG. 10 is a graphical illustration of a three-dimensional surface according to the present invention.

Cross-sections of such a three-dimensional surface may be identified on the aforedescribed slices. Referring to FIG. 10, a single three-dimensional surface 30 is defined by corresponding paths $PATH_1$, $PATH_2$, ... $PATH_N$ (generally "PATH") lying in corresponding parallel slices $SLICE_1$, $SLICE_2$, ... $SLICE_N$ (generally "SLICE") of the space 11.

Each PATH is determined by all of the paths lying on the corresponding SLICE. For example, FIG. 4 shows two paths "C" and "D" corresponding to a SLICE referred to above as slice 21. According to the invention, a new PATH would be created for the slice 21 that splits the difference between the paths "C" and "D."

Figure 11:
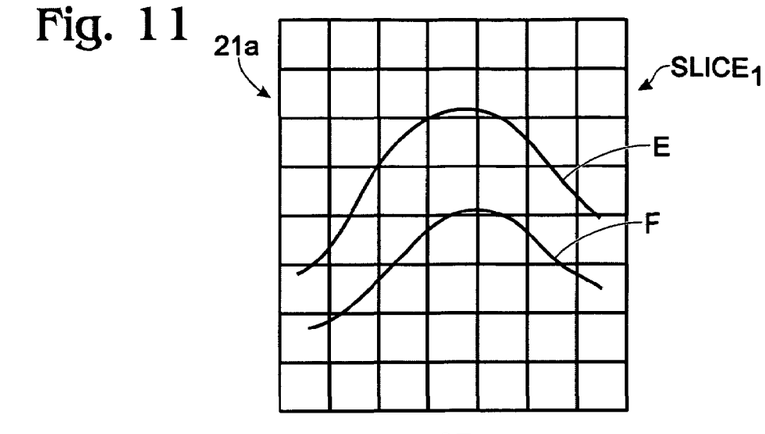
FIG. 11 is a pictorial view of the slice of FIG. 4 partitioned into cellular areas according to the present invention and showing two paths of the hand-held device of FIG. 1 that lie on the slice and that pass through the cellular areas.
Figure 12:
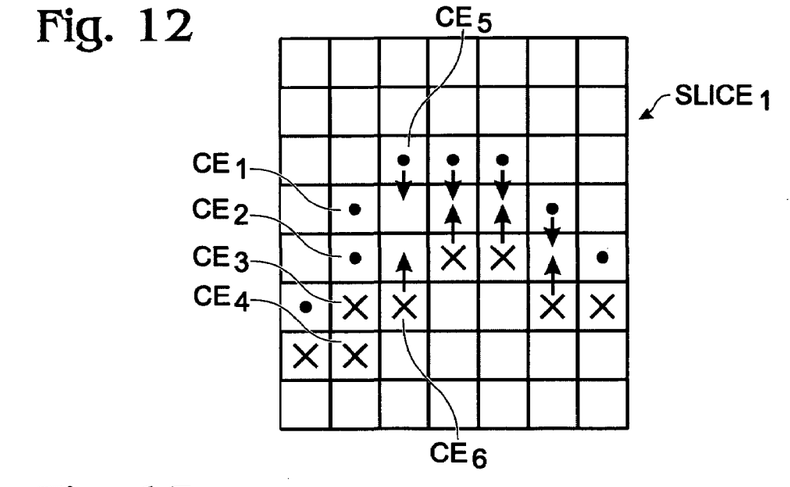
FIG. 12 is the same view of the slice as shown in FIG. 11 with positions on the paths quantized within the cellular areas according to the present invention, and showing an example of movements of the quantized positions of the two paths according to the present invention.
Figure 13:
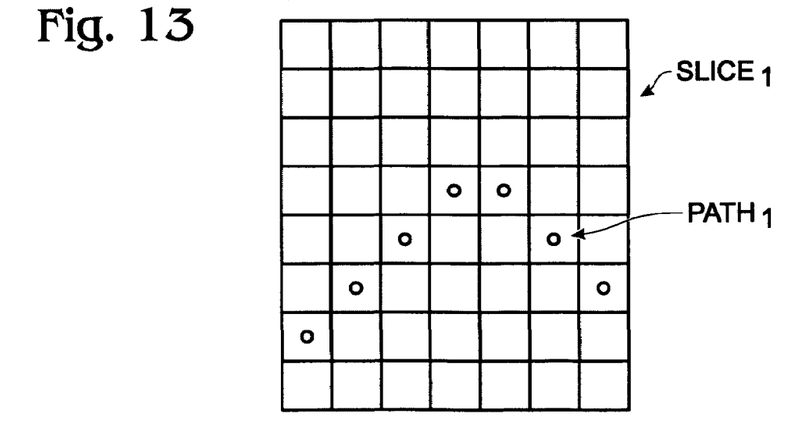
FIG. 13 is the same view of the slice as shown in FIG. 11 showing quantized positions for a single path resulting from the movements of FIG. 12, for use in developing the surface of FIG. 10 according to the present invention.

Turning to FIG. 11, two paths "E" and "F" are shown lying on the slice $SLICE_1$ of FIG. 10. The slice $SLICE_1$ is partitioned into cellular areas 21a. The paths "E" and "F" represent two separate passes of the hand-held device. Quantized positions for the two paths within the cellular areas are shown in FIG. 12, the positions of the path "E" being indicated by the symbol • while the positions of the path "F" are indicated by the symbol X. Up and down arrows indicate how the difference between the two paths may be split. Where, as for the cellular areas $CE_1$ and $CE_2$, corresponding to the path "E," and the cellular areas $CE_3$ and $CE_4$, corresponding to the path "F," or as for the cellular areas $CE_5$ and $CE_6$, there is not a cellular area that splits the difference, a rule can be invoked to break the tie, e.g., to select the closest lower-most cellular area such as shown in FIG. 13. Here, a new path $PATH_1$ is created as indicated by the symbol ○ by combining the paths "E" and "F." Where there are additional positions corresponding to additional paths, a weighting may be used. Paths may also be combined in other desired ways.

Similarly, additional PATHs can be generated for the remaining SLICEs to construct the surface indicated in FIG. 10. The three-dimensional surface can be used to provide a graphic indication of the location of the disturbance determined as described above. Particularly, the computer 8 may generate the surface and display, for example, either a specific location for the disturbance, or the histogram counts showing dispersion of the probability associated with the disturbance in relation to the surface.

The usefulness of the reference surface as a graphical visualization aid can be increased by intentionally moving the device 10 so that it conforms to physical landmarks. For example, where the passes of the device 10 are intentionally held in close conformance to the body of the patient 13 of FIG. 2, e.g., within about 3 inches, the three-dimensional surface provides a body contour. A body contour, when displayed along with the location of an indicated surgical instrument left inside the same body, provides a best reference for the surgeon to use in judging where to enter the body to retrieve the instrument. Close conformance to a target volume in which a disturbance is located may be defined generally for this purpose as being within about 10-20% of the extent of the target volume in the direction along which conformance is being measured.

All of the aforedescribed processing can be and preferably is performed outside of the hand-held device 10, in a remote computer or other data processing device 8 (see FIG. 1 and note that for graphics display, a suitable graphics display device is coupled to the device 8). This facilitates portability of the hand-held device. The hand-held device is or can be coupled to the computer 8 via a LINK that may be wired or wireless. While data collection and storage of data into the memory 26 in the hand-held device occurs in substantially real time, the processing may be performed in the computer 8 at a later time and over a longer duration if necessary. However, it should be understood that the computational and analytical functionality described above could be implemented in any desired combination of hardware and software.

It should be understood that, while a specific method and apparatus for collecting data for use in detecting and locating disturbances has been shown and described as preferred, other configurations and methods could be utilized, in addition to those already mentioned, without departing from the principles of the invention.

The terms and expressions which have been employed in the foregoing specification are used therein as terms of description and not of limitation, and there is no intention in the use of such terms and expressions to exclude equivalents of the features shown and described or portions thereof, it being recognized that the scope of the invention is defined and limited only by the claims which follow.

The invention claimed is:

1. A method for detecting a physical disturbance in a space, the method comprising:
providing a sensing device having an inertial guidance system;
moving the device through the space and obtaining therewith a plurality of sets of position data representing positions of the device determined by the inertial guidance system and sensed data representing a physical characteristic of the space at said positions;
identifying, within the space, distinct regions thereof;
quantizing, for each of said regions, the positions therein, where at least one of said regions has associated therewith at least two of said positions;
combining, for each of said regions, the sensed data associated with the quantized positions therein; and
providing results data representing at least the presence or absence of the disturbance, the results data being based, at least in part, on the result of said step of combining.

2. The method of claim 1, wherein said regions of space form a regular lattice.

3. The method of claim 1, wherein said step of combining includes averaging, for each of said regions, the sensed data associated with the quantized positions therein.

4. The method of claim 1, wherein the sensed data are representative of magnetic permeability.

5. The method of claim 1, wherein the sensed data are representative of an electromagnetically transmitted code.

6. The method of claim 1, wherein said results data represent one or more possible locations of the disturbance, the method further comprising displaying a graphical indication of said one or more possible locations to a user.

7. A method for detecting a physical disturbance in a space, the method comprising:
moving a sensing device through the space in a first pass and obtaining therewith first sets of first position data representing first positions of the device and first sensed data representing a first physical characteristic of the space at said first positions in a baseline condition of the space so as to define baseline scan results;
moving said device through space in a second pass distinct from said first pass to obtain second sets of position data representing second positions of the device and second sensed data representing a second physical characteristic of the space at said second positions in a potentially disturbed condition of the space so as to define test scan results;
identifying, within the space, distinct regions thereof;
quantizing, for each of said regions, the positions therein, where at least one of said regions has associated therewith at least two of said positions;
combining, for each of said regions having associated baseline scan results, the baseline scan results associated with the quantized positions therein, defining combined, quantized baseline scan results;

combining, for each of said regions having associated test scan results, the test scan results associated with the quantized positions therein, defining combined, quantized test scan results;

forming respective data of the difference between the combined, quantized test scan results and the combined, quantized baseline scan results, defining ultimate data associated with said regions; and providing results data representative of at least the presence or absence of the disturbance, the results data being based at least in part on evaluating whether the ultimate data corresponding to at least one said regions exceeds a threshold.

8. The method of claim 7, further comprising providing, in the device, an inertial guidance system for determining the positions.

9. The method of claim 8, further comprising, if the result of said step of evaluating is that the ultimate data corresponding to at least one of said regions exceeds said threshold, providing an indication to an operator that the disturbance has occurred in the space.

10. The method of claim 7, further comprising, if the result of said step of evaluating is that the ultimate data corresponding to at least one of said regions exceeds said threshold, determining a location for the disturbance within a subset of said regions.

11. The method of claim 10, further comprising providing, in the device, an inertial guidance system for determining the positions.

12. The method of claim 11, wherein said step of determining further comprises identifying one of said regions that represents a most likely portion of the space in which the disturbance has occurred.

13. The method of claim 12, wherein said regions of space form a regular lattice.

14. The method of claim 12, wherein said steps of combining include, respectively, spatially averaging, for regions having associated baseline scan results, the baseline scan results associated with the quantized positions therein, and, for regions having associated test scan results, the test scan results associated with the quantized positions therein.

15. The method of claim 12, wherein the first and second sensed data are responsive to magnetic permeability.

16. The method of claim 12, wherein the first and second sensed data are responsive to an electromagnetically transmitted code.

17. The method of claim 10, further comprising displaying a graphical indication of said location to a user.

18. The method of claim 7, further comprising:

identifying a first set of said ultimate data corresponding to at least two of said regions;

triangulating one or more possible locations of said disturbance in the space using said first set; and displaying a graphical indication of said one or more possible locations to a user.

19. The method of claim 18, further comprising identifying a second set of said ultimate data corresponding to at least one more of said regions, wherein said step of triangulating uses both said first and second sets of data.

20. The method of claim 19, further comprising providing, in the device, an inertial guidance system for determining the positions.

21. The method of claim 18, further comprising providing, in the device, an inertial guidance system for determining the positions.

22. The method of claim 18, wherein said step of identifying identifies at least first and second sets of said ultimate data corresponding to a planar slice of the space, and wherein said step of triangulating includes at least determining first and second loci of said possible locations lying in said slice and corresponding, respectively, to said first and second sets.

23. The method of claim 22, further comprising providing, in the device, an inertial guidance system for determining the positions.

24. The method of claim 22, further comprising:

counting, for each of said regions having associated possible locations, the number of possible locations associated therewith; and identifying one or more of said regions in which the location of the disturbance is most likely by determining for which of said regions said counting produces a higher value than is produced for other said regions.

25. The method of claim 24, further comprising providing, in the device, an inertial guidance system for determining the positions.

26. The method of claim 24, wherein said regions of space form a regular lattice.

27. The method of claim 24, wherein said steps of combining include, respectively, spatially averaging, for regions having associated baseline scan results, the baseline scan results associated with the quantized positions therein, and, for regions having associated test scan results, the test scan results associated with the quantized positions therein.

28. The method of claim 24, wherein the sensed data are responsive to magnetic permeability.

29. The method of claim 24, wherein the sensed data are responsive to an electromagnetically transmitted code.

30. The method of claim 18, wherein said regions of space form a regular lattice.

31. The method of claim 18, wherein said steps of combining include respectively, spatially averaging, for regions having associated baseline scan results, the baseline scan results associated with the quantized positions therein, and, for regions having associated test scan results, the test scan results associated with the quantized positions therein.

32. The method of claim 18, wherein the sensed data are responsive to magnetic permeability.

33. The method of claim 18, wherein the sensed data are responsive to an electromagnetically transmitted code.

34. The method of claim 18, further comprising producing a three-dimensional surface representation of said positions and displaying said three-dimensional surface representation along with said one or more possible locations of the disturbance.

35. The method of claim 7, wherein said results data represent one or more possible locations of the disturbance, the method further comprising displaying a graphical indication of said one or more possible locations to a user.

36. A method for detecting a physical disturbance in a space, the method comprising:

moving a sensing device through the space in a first pass and obtaining therewith first sets of first position data representing first positions of the device and first sensed data representing a first physical characteristic of the space at said first positions in a baseline condition of the space so as to define baseline scan results;

moving said device through space in a second pass distinct from said first pass to obtain second sets of position data representing second positions of the device and second sensed data representing a second physical characteristic of the space at said second positions in a potentially disturbed condition of the space so as to define test scan results;

identifying, within the space, distinct regions thereof;

quantizing, for each of said regions, the positions therein;

combining, for each of said regions having associated baseline scan results, the baseline scan results associated with the quantized positions therein, defining combined, quantized baseline scan results;

combining, for each of said regions having associated test scan results, the test scan results associated with the quantized positions therein, defining combined, quantized test scan results;

forming respective data of the difference between the combined, quantized test scan results and the combined, quantized baseline scan results, defining ultimate data associated with said regions; and providing results data representative of at least the presence or absence of the disturbance, the results data being based at least in part on evaluating whether the ultimate data corresponding to at least one said regions exceeds a threshold.

37. The method of claim 36, further comprising providing, in the device, an inertial guidance system for determining the positions.

38. The method of claim 37, further comprising, if the result of said step of evaluating is that the ultimate data corresponding to at least one of said regions exceeds said threshold, providing an indication to an operator that the disturbance has occurred in the space.

39. The method of claim 36, further comprising, if the result of said step of evaluating is that the ultimate data corresponding to at least one of said regions exceeds said threshold, determining a location for the disturbance within a subset of said regions.

40. The method of claim 39, further comprising providing, in the device, an inertial guidance system for determining the positions.

41. The method of claim 40, wherein said step of determining further comprises identifying one of said regions that represents a most likely portion of the space in which the disturbance has occurred.

42. The method of claim 41, wherein said regions of space form a regular lattice.

43. The method of claim 41, wherein said steps of combining include, respectively, spatially averaging, for regions having associated baseline scan results, the baseline scan results associated with the quantized positions therein, and, for regions having associated test scan results, the test scan results associated with the quantized positions therein.

44. The method of claim 41, wherein the first and second sensed data are responsive to magnetic permeability.

45. The method of claim 41, wherein the first and second sensed data are responsive to an electromagnetically transmitted code.

46. The method of claim 39, further comprising displaying a graphical indication of said location to a user.

47. The method of claim 36, further comprising:

identifying a first set of said ultimate data corresponding to at least two of said regions;

triangulating one or more possible locations of said disturbance in the space using said first set; and displaying a graphical indication of said one or more possible locations to a user.

48. The method of claim 47, further comprising identifying a second set of said ultimate data corresponding to at least one more of said regions, wherein said step of triangulating uses both said first and second sets of data.

49. The method of claim 48, further comprising providing, in the device, an inertial guidance system for determining the positions.

50. The method of claim 47, further comprising providing, in the device, an inertial guidance system for determining the positions.

51. The method of claim 47, wherein said step of identifying identifies at least first and second sets of said ultimate data corresponding to a planar slice of the space, and wherein said step of triangulating includes at least determining first and second loci of said possible locations lying in said slice and corresponding, respectively, to said first and second sets.

52. The method of claim 51, further comprising providing, in the device, an inertial guidance system for determining the positions.

53. The method of claim 51, further comprising:

counting, for each of said regions having associated possible locations, the number of possible locations associated therewith; and identifying one or more of said regions in which the location of the disturbance is most likely by determining for which of said regions said counting produces a higher value than is produced for other said regions.

54. The method of claim 53, further comprising providing, in the device, an inertial guidance system for determining the positions.

55. The method of claim 53, wherein said regions of space form a regular lattice.

56. The method of claim 53, wherein said steps of combining include, respectively, spatially averaging, for regions having associated baseline scan results, the baseline scan results associated with the quantized positions therein, and, for regions having associated test scan results, the test scan results associated with the quantized positions therein.

57. The method of claim 53, wherein the sensed data are responsive to magnetic permeability.

58. The method of claim 53, wherein the sensed data are responsive to an electromagnetically transmitted code.

59. The method of claim 47, wherein said regions of space form a regular lattice.

60. The method of claim 47, wherein said steps of combining include, respectively, spatially averaging, for regions having associated baseline scan results, the baseline scan results associated with the quantized positions therein, and, for regions having associated test scan results, the test scan results associated with the quantized positions therein.

61. The method of claim 47, wherein the sensed data are responsive to magnetic permeability.

62. The method of claim 47, wherein the sensed data are responsive to an electromagnetically transmitted code.

63. The method of claim 47, further comprising producing a three-dimensional surface representation of said positions and displaying said three-dimensional surface representation along with said one or more possible locations of the disturbance.

64. The method of claim 36, wherein said results data represent one or more possible locations of the disturbance, the method further comprising displaying a graphical indication of said one or more possible locations to a user.

65. A method for detecting a physical disturbance in a space, the method comprising:

providing a sensing device having an inertial guidance system;

moving the device through the space and obtaining therewith a plurality of sets of position data representing positions of the device determined by the inertial guidance system and sensed data representing a physical characteristic of the space at said positions;

identifying, within the space, distinct regions thereof;

quantizing, for each of said regions, the positions therein, where at least one of said regions has associated therewith at least two of said positions;

combining, for each of said regions, the sensed data associated with the quantized positions therein; and providing results data representing at least the presence or absence of the disturbance, the results data being based, at least in part, on the result of said step of combining, wherein said step of combining includes averaging, for each of said regions, the sensed data associated with the quantized positions therein.

* * * * *